United States Patent [19]

Mogyoródi et al.

[11] Patent Number: 4,511,736

[45] Date of Patent: Apr. 16, 1985

[54] PROCESS FOR THE PREPARATION OF SUBSTITUTED CHLOROACETANILIDES

[75] Inventors: Ferenc Mogyoródi; Enikö Koppány; Tibor Bódi; Károly Balogh, all of Miskolc; István Tóth, Sajóbábony; Rezsö Bognár, Debrecen; Sándor Makleit, Debrecen; György Litkei, Debrecen; Miklós Rákosi, Debrecen; Zoltán Dinya, Debrecen, all of Hungary

[73] Assignee: Eszakmagyarorszagi Vegyimuvek, Sajóbábony, Hungary

[21] Appl. No.: 456,383

[22] Filed: Jan. 7, 1983

[30] Foreign Application Priority Data

Jan. 15, 1982 [HU] Hungary .................. 103/82

[51] Int. Cl.³ .................. C07C 102/00; C07C 102/06
[52] U.S. Cl. .................. 564/214; 564/133; 564/143
[58] Field of Search .................. 564/214, 133, 143; 71/118

[56] References Cited

U.S. PATENT DOCUMENTS

| | | | |
|---|---|---|---|
| 2,863,752 | 12/1958 | Hamm et al. | 564/214 X |
| 4,168,965 | 9/1979 | Vogel et al. | 564/214 X |
| 4,283,221 | 8/1981 | Vogel et al. | 564/214 X |
| 4,284,564 | 8/1981 | Alt et al. | 564/214 X |
| 4,334,909 | 6/1982 | Chupp | 564/214 X |
| 4,399,306 | 8/1983 | Pintér et al. | 564/214 |

FOREIGN PATENT DOCUMENTS 103351 6/1983 Japan .................. 564/214

Primary Examiner—Thomas A. Waltz
Attorney, Agent, or Firm—Karl F. Ross; Herbert Dubno

[57] ABSTRACT

The invention relates to a novel process for preparing chloroacetanilides of the formula

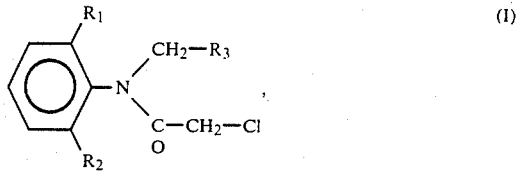

wherein:
$R_1$ and $R_2$ represent independently from each other a hydrogen atom or a $C_{1-8}$ alkyl or $C_{1-8}$ alkoxy group; and
$R_3$ stands for a straight chained or branched $C_{1-8}$ alkoxy group.

Said process is characterized by chloroacetylating a 2,6-dialkylaniline of the formula

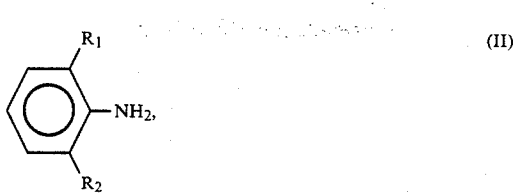

wherein $R_1$ and $R_2$ are as defined above, at a temperature of 10° to 120° C., optionally in a solvent medium in the presence of an acid binding agent, then reacting a thus-obtained intermediate with chloromethyl chloroformiate or, alternatively, reacting a compound of the formula (II) first with chloromethyl chloroformiate and subjecting then to chloroacetylation, thereafter reacting a thus-obtained intermediate with an alcohol of the formula $R_3$—OH (III), wherein $R_3$ is as defined above, optionally in a solvent medium in the presence of an acid binding agent, and recovering a product of the formula (I) in a known manner.

The process of the invention enables the more simple and economic preparation of the compounds of formula (I) of improved purity.

10 Claims, No Drawings

PROCESS FOR THE PREPARATION OF SUBSTITUTED CHLOROACETANILIDES

SPECIFICATION

The invention relates to a novel process for the preparation of substituted chloroacetanilides of the formula

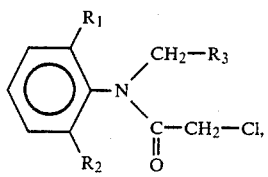

wherein:

$R_1$ and $R_2$ represent independently from each other a hydrogen atom a $C_{1-8}$ alkoxy or alkyl group; and $R_3$ is a straight chain or branched $C_{1-8}$ alkoxy group.

Several substituted chloroacetanilides of the formula (I) have been used in the past years as active components of selective herbicidal compositions due to their respective biological activity. Several processes have been developed for the preparation of these biologically active compounds.

For example, according to the U.S. Pat. Nos. 3,442,945, 3,547,620 and 3,630,716 a N-methylene-2,6-dialkylaniline is reacted with chloroacetylchloride in an organic solvent such as n-heptane and the thus-obtained N-chloroacetyl-N-chloromethyl-2,6-dialkylaniline is reacted, without isolation or after isolation and purification, with a corresponding alcohol in the presence of an acid binding agent such as triethyl amine. After the termination of the reaction the products are purified from the contaminants by aqueous washing, distillation and crystallization. The main drawback of this process resides in the low yield which is due, on the one hand, to the complicated synthesis route and reaction conditions and, on the other hand, to the relatively complicated purification process needed to obtain a product of adequate purity. Moreover, the necessity of an aqueous washing is accompanied by the formation of substantial amounts of waste water which represent environmental problems.

A similar process is described in the Hungarian patent specification No. 176,581 with the difference that the reactions are carried out in an inert atmosphere and in the presence of ammonia as acid binding agent.

When performing the process described in said Hungarian specification a N-methylene-2,6-dialkylaniline is added to chloroacetyl chloride under stirring and cooling, then the reaction mixture is heated to 90° C. and after stirring for 0.5 hours at this temperature it is cooled back to 25° C. The reaction mixture is flushed with nitrogen and a corresponding amount of a dry alcohol is added thereto. The reaction mixture is thereafter treated with gaseous ammonia at 35° to 40° C. and after the end of this treatment it is heated at 85° C. for 0.5 hours. The reaction mixture is cooled back, washed with water and the phases are separated. The organic phase is evaporated in vacuo by giving the final product in a yield of 84 to 85%.

This process is apparently similar to the previous one as regards the complicated reaction sequences due to the fact that both processes start from the Schiff base, i.e. a N-methylene-2,6-dialkylamine.

It is known in the art that N-methylene-2,6-dialkylanilines can be prepared by reacting a 2,6-dialkylaniline with formaldehyde. This latter compound is prepared generally by depolymerizing paraformaldehyde in absolute methanol in the presence of triethyl amine. The thus-formed N-methylene-2,6-dialkylanilides are purified, and, can be, dewatered by distilling in vacuo, whereafter they are either reacted further immediately or stored under nitrogen atmosphere.

The invention provides a novel process for the preparation of the substituted chloroacetanilides of the formula

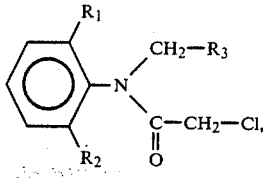

wherein:

$R_1$ and $R_2$ represent independently from each other a hydrogen atom or a $C_{1-8}$ alkyl or $C_{1-8}$ alkoxy group; and $R_3$ stands for a straight chain or branched $C_{1-8}$ alkoxy group, which is simpler, more economical and more apt to produce a pure product than the earlier processes.

The essence of the invention is that an aniline of the formula

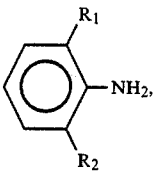

wherein $R_1$ and $R_2$ are as defined above, is transformed into a corresponding N-chloroacetanilide by using chloroacetyl chloride, said 2,6-dialkyl-N-chloroacetanilide is acylated with chloromethyl chloroformiate and a thus-obtained N-chloroacetyl-N-chloromethylaniline is reacted with an alcohol of the formula $$R_3\text{—H} \qquad (III),$$

wherein $R_3$ is as defined above, optionally in the presence of an acid binding agent. A thus-obtained N-chloroacetyl-N-alkoxymethyl-2,6-dialkylanilide of the formula (I) can be isolated and purified by methods well known in the art.

According to a further feature of the present invention an aniline of the formula (II) is first acylated with chloromethyl chloroformiate and then with chloroacetyl chloride and finally a thus-obtained intermediate is reacted with an alcohol of the formula (III).

According to a still further feature of the invention an aniline is converted into a N-chloroacetyl-2,6-dialkylanilide by using monochloroacetic acid and phosphorous trichloride or an other chlorinating agent such as thionyl chloride or phosgene, whereafter said intermediate is reacted further as described before.

According to a still further feature of the invention first in an appropriate reactor chloroacetyl chloride is prepared from monochloroacetic acid and phosphorous chloride or phosgene or any other chlorinating agent, then is added into the reactor and a thus-obtained intermediate N-chloroacetylaniline is first reacted with chloromethyl chloroformiate and then with a corresponding alcohol of the formula (III) as described before.

The main advantage of the process of the invention are as follows:

(a) As starting material no N-methylene-aniline is used wherefore it is not necessary to use paraformaldehyde or formaldehyde and methanol and to perform several difficult steps to purify and use N-methylene-anilines.

(b) The process of the invention can be performed even in the case no chloroacetyl chloride and paraformaldehyde are available.

The invention should be elucidated in detail by the aid of the following non-limiting examples.

EXAMPLE 1

118 g. of chloroacetyl chloride are metered into a reactor, then it is heated to 60° C. and 149.0 g of 2,6-diethylaniline are added thereto. The reaction mixture is heated to 80° C. and held at this temperature for an hour.

4.70 g. of dimethyl formamide are added to the reaction mixture at 80° C. and then 159.0 g of chloromethyl chloroformiate are dropped thereto within 1.5 hours. The reaction mixture is heated to 90° C. and held at this temperature for three hours.

The reaction mixture is then added to 320.0 g of methanol, while maintaining the temperature thereof below 60° C. After stirring at 60° C. for 0.5 hours the reaction mixture is cooled, 160 g. of methanol are removed by distilling in vacuo and the little amount of the precipitated solids is removed by filtering. The product N-methoxymethyl-2,6-diethyl-chloroacetanilide being dissolved is either used in the form of a solution or crystallized by removing the solvent.

Recovered material: 256 g.
Active agent contents: 88%.
Yield: 84.5%.
Melting point: 41°–41.5° C.

EXAMPLE 2

158 g. of chloromethyl chloroformiate and 86 g. of xylene are heated to 80° C. and 149 g. of 2,6-dimethylaniline are added dropwise. Then the reaction mixture is heated to a temperature of 100° to 105° C. and held at this temperature as long as it becomes clear, i.e. for about 2 to 2.5 hours. Thereafter 4.7 g of dimethyl formamide and 118 g. of chloroacetyl chloride are added dropwise and after storing at 100° C. for 4 hours the reaction mixture is poured into 320 g. of methanol while maintaining the temperature thereof below 60° C. After stirring at 60° C. for half an hour, the reaction mixture is cooled to 20° C. and 240 g. of methanol are removed by distilling in vacuo. The little amount of the precipitated solid material is removed by filtering. The product N-methoxymethyl-2,6-dimethyl-chloroacetanilide being dissolved is either used in the form of a solution or it is crystallized by removing the solvent.

Recovered material: 262 g.
Active agent contents: 84%.
Yield: 82%.
Refractive index $n_D^{25} = 1.4938$.

EXAMPLE 3

97 g. of monochloroacetic acid are metered into a reactor and 149 g. of 2,6-diethylaniline and 1.8 g. of dimethyl formamide are dropped thereto. The reaction mixture is heated to 80° to 85° C. and phosgene is introduced at a speed of 50 g./hour for two hours.

158 g. of chloromethyl chloroformiate are added to the reaction mixture in half an hour at 80° C. and then it is held at 90° C. for three hours.

The reaction mixture is then added to 320 g. of methanol, while maintaining the temperature thereof below 60° C. After stirring at 60° C. for 0.5 hours the reaction mixture is cooled and 160 g. of methanol are removed by distilling in vacuo. The little amount of the precipitated solid material is removed by filtration. The product N-methoxymethyl-2,6-diethyl-chloroacetanilide being dissolved is either used in the form of a solution or crystallized by removing the solvent.

Recovered material: 275 g.
Active agent contents: 83.8%.
Yield: 85%.
Melting point: 41°–41.5° C.

EXAMPLE 4

97 g. of monochloroacetic acid and 2.7 g. of dimethyl formamide are metered into a reactor and after heating to 100° C. the reaction mixture is converted into chloroacetyl chloride by introducing phosgene for two hours at a speed of 50 g./hour.

After cooling to 80° C. 149 g. of 2,6-diethylaniline are added and the reaction mixture is held at this temperature for an hour. Dimethyl formamide is added thereto again, in this case in an amount of 4.5 g. Thereafter 158 g. of chloromethyl chloroformiate are added within 1.5 hours, the mixture is heated to 90° C., held at this temperature for 3 hours. Then it is poured into 320 g. of methanol, while maintaining the temperature thereof below 60° C. After storing at 60° C. for half an hour 160 g. of methanol are removed by distilling the vacuo. After cooling the precipitated solid substance is filtered off. The product N-methoxymethyl-2,6-diethyl-chloroacetanilide being dissolved is either used in the form of a solution or crystallized by removing the solvent.

Recovered material: 263 g.
Active agent contents: 84.1%.
Yield: 82%.
Melting point: 41°–41.5° C.

EXAMPLE 5

118 g. of chloroacetyl chloride are metered into a reactor, then it is heated to 60° C. and 135.2 g. of 2-ethyl-6-methylaniline are added thereto. The reaction is performed at 80° C., the reaction mixture is held at this temperature for an hour. After adding 4.5 g. of dimethyl formamide 158 g. of chloromethyl chloroformiate are dropped into the reaction mixture within 1.5 hours.

The reaction mixture is held at 90° C. for 3 hours, then poured into 320 g. of ethanol, while maintaining the temperature thereof below 60° C. After stirring at 60° C. for half an hour the reaction mixture is cooled and 160 g. of ethanol is removed by distilling in vacuo. The little amount of the precipitated solid substance is filtered off. The product 2-methyl-6-ethyl-N-ethoxymethyl-chloroacetanilide being dissolved is either used in the form of a solution or crystallized by removing the solvent.

Recovered material: 251 g.
Active agent contents: 89%.
Yield: 83%.
Refractive index $n_D{}^{25} = 1.5233$.

EXAMPLE 6

97 g. of monochloroacetic acid are metered into a reactor, then 135.2 g. of 2-methyl-6-ethylaniline and 1.8 g. of dimethyl formamide are added. The reaction mixture is heated to 80° to 85° C. and phosgene is introduced therein for two hours at a speed of 50 g./hour. Then 158 g. of chloromethyl chloroformiate are dropped at 80° C. within half an hour and then the mixture is held at 90° C. for 3 hours.

The reaction mixture is then added into 320 g. of ethanol while keeping the temperature below 60° C.

After stirring at 60° C. the reaction mixture is cooled and 160 g. of ethanol are removed by distilling in vacuo. The little amount of the precipitated solid material is filtered off.

The product N-ethoxymethyl-2-methyl-6-ethyl chloroacetanilide being dissolved is either used in the form of a solution or crystallized by removing the solvent.

Recovered material: 259 g.
Active agent contents: 89%.
Yield: 86%.
Refractive index $n_D{}^{25} = 1.5233$.

EXAMPLE 7

97 g. of monochloroacetic acid and 2.7 g. of dimethyl formamide are metered into a reactor and after heating to 100° C. the reaction mixture is converted into chloroacetyl chloride by introducing phosgene for two hours at a speed of 50 g./hour.

The reaction mixture is cooled to 80° C. and 135.2 g. of 2-ethyl-6-methylaniline are added thereto. The mixture is kept at this temperature for an hour and after adding 4.5 g. of dimethyl formamide 158 g. of chloromethyl chloroformiate are metered thereto within 1.5 hours, then after heating to 90° C. it is held at this temperature for 3 hours.

The reaction mixture is then added to 320 g. of ethanol, while maintaining the temperature thereof below 60° C. After half an hour it is cooled to 20° C. and 160 g. of ethanol are removed by distilling in vacuo.

The residue is cooled and the little amount of precipitate is filtered off.

The product N-ethoxymethyl-2-methyl-6-ethyl-chloroacetanilide being dissolved is either used in the form of a solution or crystallized by removing the solvent.

Recovered material: 263 g.
Active agent contents: 85%.
Yield: 83%.
Refractive index $n_D{}^{25} = 1.5233$.

EXAMPLE 8

118 g. of chloroacetyl chloride are metered into a reactor at a temperature of 60° C. and 149 g. of 2,6-diethylaniline are added thereto. The reaction mixture is held at this temperature for an hour.

Then 4.5 g. of dimethyl formamide are added and thereafter 158 g. of chloromethyl chloroformiate are dropped into the reaction mixture within 1.5 hours and it is held at 90° C. for three hours.

The reaction mixture is added into 400 g. of n-butanol, while maintaining the temperature below 60° C. After keeping at 80° C. for 4 hours it is cooled and 240 g. of solvent are removed by distilling in vacuo.

The product being dissolved is either crystallized by removing the solvent or used in the form of a solution.

Recovered material: 300 g.
Active agent contents: 81%.
Yield: 79%.
Boiling point: 196° C./0.5 mmHg.
Refractive index $n_D{}^{25} = 1.5163$.

EXAMPLE 9

97 g. of monochloroacetic acid are metered into a reactor, 149 g. of 2,6-diethylaniline and 4.5 g. of dimethyl formamide are dropped thereto and after heating to a temperature of 80° to 85° C. phosgene is introduced into the reaction mixture for two hours at a speed of 50 g./hour.

Then 158 g. of chloromethyl chloroformiate are added to the mixture at 80° C. within half an hour and it is held at 90° C. for three hours.

Thereafter the reaction mixture is added to the mixture of 101 g. of triethylamine and 160 g. of n-butanol, while maintaining the temperature thereof below 60° C. After stirring for half an hour the reaction mixture is cooled to 20° C., filtered off, washed twice with water and separated, then it is dehydrated or a little amount of solvent is removed by distilling in vacuo.

The thus-obtained substance is used further in this form or it is crystallized after removing the solvent.

Recovered material: 302 g.
Active agent contents: 83.5%.
Yield: 85%.
Boiling point: 196° C./0.5 mmHg.
Refractive index $n_D{}^{25} = 1.5163$.

EXAMPLE 10

118 g. of chloroacetyl chloride are metered into a reactor, it is heated to 60° C. and after adding 149 g. of 2,6-diethylaniline the reaction mixture is held at 80° C. for an hour. Then 4.5 g. of dimethyl formamide and 158 g. of chloromethyl chloroformiate are added to the reaction mixture within 1.5 hours.

Then the reaction mixture is stirred at 90° C. for three hours. As soon as the reaction terminated the substance is added to the mixture of 160 g. of n-propanol and 101 g. of triethylamine under stirring. A temperature of 60° C. should be maintained during this step.

The reaction mixture is stirred for half an hour, cooled back, the triethylamine-hydrochloride is filtered off, the organic phase is washed with 100 ml. of water and dehydrated by distilling in vacuo.

Recovered material: 289 g.
Active agent contents: 89%.
Yield: 84.5%.
Boiling point: 100° C./$10^{-3}$ mm Hg.
Refractive index $n_D{}^{25} = 1.5193$.

EXAMPLE 11

118 g. of chloroacetyl chloride are metered into a reactor, heated to 60° C. and after adding 149 g. of 2,6-diethylaniline the reaction mixture is held at 80° C. for an hour.

Then 4.5 g. of dimethyl formamide are added thereto and 158 g. of chloromethyl chloroformiate are dropped within 1.5 hours. The reaction mixture is held at 80° C. for three hours.

Then the reaction mixture is added to the mixture of 165 g. of octanol and 101 g. of triethylamine under stirring.

The alcoholysis takes place at a temperature of 60° C., the reaction mixture is held at this temperature for four hours.

After cooling the triethylamine hydrochloride is filtered off. The organic phase is washed with 100 ml of water, separated and dehydrated by distilling in vacuo.

Recovered material: 341 g.
Active agent contents: 82%.
Yield: 83%.
Refractive index $n_D^{25} = 1.5239$.

What is claimed is:

1. A process for the preparation of a substituted chloroacetanilide of the formula

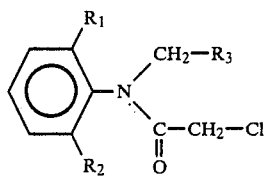 (I)

wherein:
R<sub>1</sub> and R<sub>2</sub> represent independently from each other a hydrogen atom or a $C_{1-8}$ alkyl or $C_{1-8}$ alkoxy group; and
R<sub>3</sub> is a straight chain or branched $C_{1-8}$ alkoxy group comprising the steps of chloroacetylating an aniline of the formula

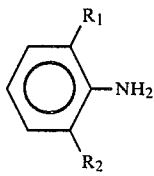 (II)

at a temperature of 10° to 120° C., optionally in a solvent medium in the presence of an acid binding agent, then reacting a thus-obtained intermediate with chloromethyl chloroformiate or, alternatively, reacting a compound of the formula (II) first with chloromethyl chloroformiate and subjecting the product to chloroacetylation, thereafter reacting a thus-obtained intermediate with an alcohol of the formula $R_3$—H  (III)

optionally in a solvent medium in the presence of an acid binding agent, and recovering a product of the formula (I).

2. A process as claimed in claim 1, characterized by first chloroacetylating an aniline of the formula (II) and then reacting the corresponding intermediate with chloromethyl chloroformiate.

3. A process as claimed in claim 1, characterized by reacting first an aniline of the formula (II) with chloromethyl chloroformiate and then chloroacetylating the thus-obtained intermediate.

4. A process as claimed in claim 1 wherein chloroacetyl chloride is used as chloroacetylating agent.

5. A process as claimed in claim 1 wherein a mixture of monochloroacetic acid and phosphorous trichloride is used as chloroacetylating agent.

6. A process as claimed in claim 1 wherein a mixture of monochloroacetic acid and phosphorous oxychloride is used as chloroacetylating agent.

7. A process as claimed in claim 1 wherein a mixture of monochloroacetic acid and phosphoric pentachloride is used as chloroacetylating agent.

8. A process as claimed in claim 1 wherein the chloroacetylation is carried out with a mixture of monochloroacetic acid and phosphoruos trichloride and a simultaneous introduction of gaseous chlorine.

9. A process as claimed in claim 1 wherein the chloroacetylation is carried out with monochloroacetic acid and a simultaneous introduction of phosgene.

10. A process as claimed in claim 1 wherein the chloroacetylation is carried out with monochloroacetic acid and a simultaneous introduction of diphosgene.

* * * * *